United States Patent [19]

Daniels et al.

[11] Patent Number: 4,655,746
[45] Date of Patent: Apr. 7, 1987

[54] CATHETER DEVICE

[75] Inventors: John R. Daniels, Pacific Palisades; Erik T. Engelson, Palo Alto; Garbriel B. Vegh, Danville, all of Calif.

[73] Assignee: Target Therapeutics, Los Angeles, Calif.

[21] Appl. No.: 803,816

[22] Filed: Dec. 2, 1985

[51] Int. Cl.⁴ .............................................. A61M 25/00
[52] U.S. Cl. ...................................... 604/53; 604/101; 604/164; 128/348.1
[58] Field of Search ............... 604/164, 158, 173, 101, 604/27, 39, 40, 41, 42, 43, 53; 128/144, 348.1, 328

[56] References Cited

U.S. PATENT DOCUMENTS

| 4,000,739 | 1/1977 | Stevens | 604/43 |
| 4,198,981 | 4/1980 | Sinnbeich | 604/101 X |
| 4,423,725 | 1/1984 | Baran et al. | 604/101 X |
| 4,448,188 | 5/1984 | Loeb | 604/96 X |
| 4,453,545 | 6/1984 | Inoue | 604/101 X |
| 4,545,390 | 10/1985 | Leary | 604/96 X |
| 4,573,470 | 3/1986 | Sampson et al. | 604/96 X |
| 4,573,966 | 3/1986 | Weikl et al. | 604/101 X |

Primary Examiner—Stephen C. Pellegrino
Attorney, Agent, or Firm—Ciotti & Murashige

[57] ABSTRACT

A catheter device for transferring fluid material to or from one or more selected-length segment of a vessel. The device includes first and second catheters, each having a tube with distal and proximal ends, an inflatable balloon carried on the tube, adjacent the distal tube end, and a fluid conduit for supplying the balloon, with such operatively positioned in the vessel. A central region of the second-catheter tube is axially shiftable within the first-catheter tube, allowing the balloons to be placed at desired relative positions in the vessel. Fluid is injected into the region between the two balloons through a fluid passageway formed in a channel in the first-catheter tube.

15 Claims, 6 Drawing Figures

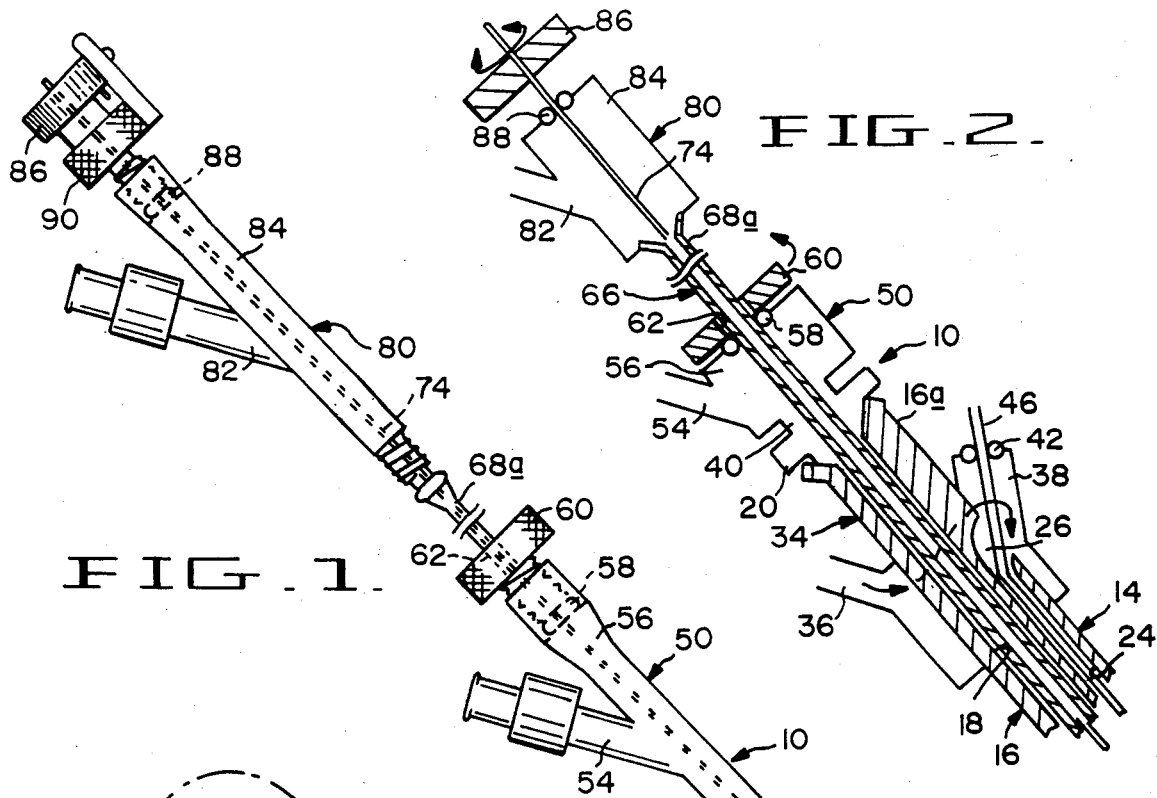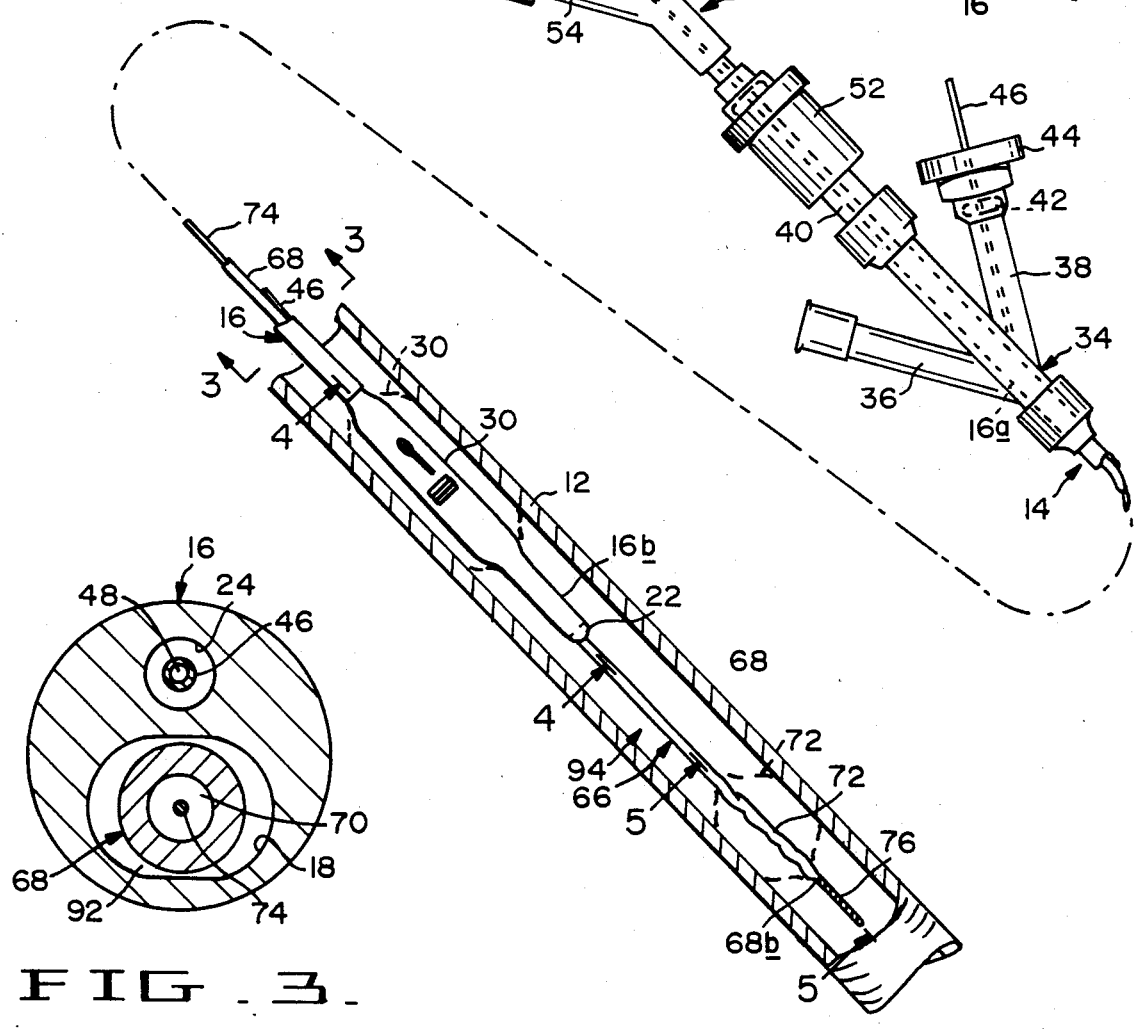

CATHETER DEVICE

FIELD OF THE INVENTION

The present invention relates to catheters, and more particularly, to a catheter for use in delivering a fluid material to a localized tissue region.

BACKGROUND OF THE INVENTION

The use of catheters to probe and treat internal body sites, via systemic routes, is becoming increasingly important in medicine. Catheters are presently used in a variety of non-surgical procedures, including blood-flow and tissue imaging by angiography, cauterizing procedures involving laser fiber optics, and localized systemic drug delivery.

Potentially, the use of catheters to inject fluid material into a localized tissue region can provide a valuable tool for treating solid cancers or other localized tissue pathologies. However, catheter methods available heretofore have generally been of limited use for this purpose. With many solid tumors (or other diseased tissue regions), the target tissue is supplied by a major artery through a group of smaller branch arteries. To deliver material into the target branch arteries using conventional procedures, a catheter is positioned in the supply artery just upstream of the target arteries, and drug is then released into the bloodstream. Since fluid flow follows the least resistance, retention of material within the larger artery is favored and a large portion of the material injected into the site will be carried downstream of the tumor site and taken up by non-tumor tissue.

The portion of an injected material which flows into the branch arteries, in the above blood-supply configuration, may be increased by occluding the major artery just downstream of the target branch arteries. The artery may be occluded conveniently by an inflatable balloon carried at the distal end of a catheter tube. This approach may still be unsatisfactory, particularly for drug delivery within a relatively long arterial segment, where the concentration of injected material may be quite variable along the length of the segment.

It may be advantageous, in delivering material to a selected tissue site, to infuse the material at a flow rate which is less than normal blood flow rate. Where the injected material is a drug, the slower infusion rate can lead to increased drug extraction by prolonging the dwell time within the tissue's vascular bed. Using catheters of the type known in the prior art, it has been difficult to achieve a controlled flow rate by injection of material into an arterial segment.

Catheters have also been used for transferring material to or from veins, for example, for sampling venous blood to determine hormone or drug levels. Often it is desired to sample venous blood from a localized tissue region, that is, a region whose venous network feeds into a defined segment of a vein. With catheters of the type available heretofore, it has been difficult to obtain such sampling.

SUMMARY OF THE INVENTION

It is therefore a general object of the invention to provide a catheter device which substantially overcomes above-mentioned problems and limitations encountered in the prior art in transferring fluid material to or from a blood vessel segment in a localized tissue region.

A related object of the invention is to provide a catheter device designed for transferring fluid material to or from an isolated vessel segment ranging in length from a few millimeters to up to several centimeters.

Still another object of the invention is to provide such a device which allows for injection of fluid material into an arterial segment at a controlled flow rate.

The catheter device of the invention includes a first catheter having a tube with distal and proximal ends, an inflatable balloon carried on the distal end of the tube, a channel extending through the tube, and a fluid conduit for supplying fluid to the balloon from the tube's proximal end. A second catheter in the device also provides a tube with distal and proximal ends, an inflatable balloon carried at the tube's distal end, and a fluid conduit for supplying fluid to the balloon from the tube's proximal end. A central region of the tube between the tube ends is slidably carried within the channel of the first-catheter tube, to allow relative axial shifting of the tubes, to place the two balloons in the device a selected axial distance from one another. A fluid passageway in one of the two tubes allows fluid transfer from the proximal end of that tube to a region between the two balloons, with the device operatively placed in a blood vessel.

In a preferred embodiment, the channel in the first-catheter tube and the outer wall of the second-catheter tube define an interlumen space which forms the fluid passageway. The proximal end of the passageway is closed by an annular seal whose sealing compression is adjustable by a thumbscrew to a compression which allows relative axial sliding movement of the two tubes.

The catheter device is intended for use in transferring fluid material to or from a selected-length segment of a vessel. In practicing the method of the invention, the first catheter is threaded into the vessel of interest until the associated balloon is positioned adjacent one end of the veseel segment. As part of the positioning procedure, the catheter may be used to deliver a contrast agent for purposes of tissue imaging. The second catheter is then threaded through the first catheter and into the vessel until its balloon is positioned adjacent the other end of the segment. Inflating the two balloons isolates the vessel segment. Fluid is then transferred through the device into or out of the isolated segment.

These and other objects and features of the invention will become more fully apparent when the following detailed description of the invention is read in conjunction with the accompanying drawings.

BRIEF DESCRIPTION OF THE DRAWINGS

FIG. 1 shows a catheter device constructed according to the invention, with a central tube portion of the device indicated by dash-dot line, and the distal end portion of the device shown within a blood vessel;

FIG. 2 illustrates, somewhat schematically, fluid-supply manifolds in the device;

FIG. 3 is an enlarged sectional view taken along section line 3—3 in FIG. 1;

DETAILED DESCRIPTION OF THE INVENTION

FIG. 1 shows a catheter device 10 constructed according to a preferred embodiment of the invention. The upper portion of the figure shows a series of manifolds in the device, to be described below, and the lower figure portion, a distal end region of the catheter carried within a segment of a blood vessel 12. The dash-dot line in FIG. 1 represents a central tubular region of the device whose actual length is typically greater than that indicated.

Figure 4:
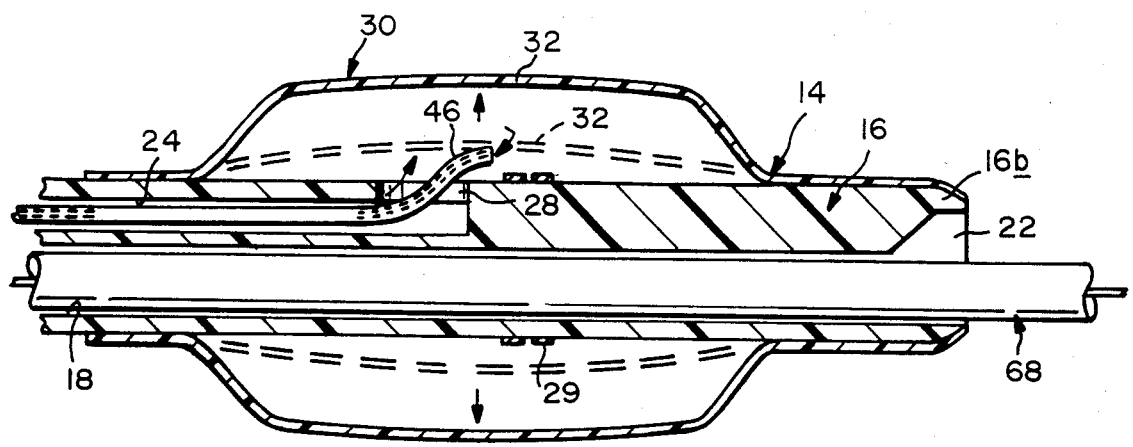
FIG. 4 is an enlarged sectional view taken along line 4—4 in FIG. 1.

Considering the construction of the device, a first catheter 14 in the device includes an elongate catheter tube 16 having proximal and distal ends or end regions 16a, 16b, respectively. With reference to the cross-sectional view in FIG. 3, the tube has an oval-shaped channel 18 which extends from a proximal opening 20 at tube end 16a (FIG. 1) to a distal opening 22 (FIG. 4) at the tube's distal end 16b. A smaller fluid conduit 24 in the tube extends through a major central region of the tube from an enlarged proximal side opening 26 (FIG. 1) to a distal side opening 28 (FIG. 4). Radio-opaque markers, such as marker 29 on the tube (FIG. 4) are used to monitor the position of the balloon fluoroscopically.

The tube is constructed and dimensioned to be threaded from a percutaneous entrance site into blood vessels whose smallest diameters are preferably between 2 and 10 mm. In a preferred device, tube 14 has a length of between about 40-140 cm, and an outer diameter of between about 50 and 150 mils. In a particular embodiment of the invention, tube 14 is about 2 feet long and has an outer diameter of 105 mils. The larger cross-sectional dimension of channel 18 is preferably about 50-70% that of the tube's outer diameter, and in the just-mentioned embodiment, is 60 mils. Conduit 24, which is used in supplying fluid to and from an inflatable balloon in the catheter, has a typical dimension of between about 20-40 mils. A tube of the type just described may be formed as an extruded polymer, such as polyethylene, according to known extrusion procedures.

A balloon 30 carried on the distal end of the tube is inflatable to form an annular expanse which is dimensioned to form a circumferential seal against the sides of the blood vessel, such as vessel 12, containing the catheter, as illustrated by dashed lines in FIG. 1. Referring to FIG. 4, the balloon is formed by sealing the opposite end regions of a flexible sleeve 32 to distal ring portions of the tube on either side of opening 28, according to conventional single-balloon catheter design. A membrane-like polyethylene sleeve is suitable. The balloon is preferably expandable to a final annular diameter of between about 2 and 10 mm for applications involving small vessels, and as large as 4 cm for applications involving large arteries. The balloon is shown in its inflated and deflated conditions in solid and dashed lines, respectively, in FIG. 4.

Referring to FIGS. 1 and 2, catheter 14 further includes a manifold 34 used in supplying fluid material to the conduit and channel in the catheter. The manifold is a conventional three-arm member having a balloon supply port 36, a vent port 38, and a central channel supply port 40. Ports 36, 40 each have a conventional fitting such as a "Luer"-type fitting, for attachment of a syringe or the like. Port 38 includes an O-ring seal 42 whose sealing diameter is adjustable by a thumbscrew 44. As seen in somewhat schematic view in FIG. 2, ports 36, 38 each communicate with conduit 24, and port 40 communicates with channel 18.

A vent wire 46 extends from its distal end within the inflatable region of balloon 30 (FIG. 4), inside conduit 24 (FIG. 3), and through port 38 and screw 44 (FIGS. 1 and 2). The wire is sealed in port 38 by tightening screw 44. The wire has a central bore 48 (FIG. 3) which provides venting when the balloon is being inflated by introducing fluid material from port 36, through conduit 24 into the balloon. The just-described catheter, including tube 14, attached balloon 30, and manifold 34 are entirely conventional and may be obtained commercially, such as from Advanced Cardiovascular Systems (Mountain View, Calif.).

Also forming part of the catheter is a two-arm manifold 50 which is attached at its lower end in FIGS. 1 and 2 to port 40 through a sealed swivel connector 52 (FIG. 1). The manifold includes a side port 54 and a central port 56, both of which communicate with (i.e., feed into) port 40, as can be appreciated from FIG. 2. The upper end of port 56 is provided with an O-ring seal 58, whose annular sealing dimension is adjustable by a thumbscrew 60. The screw has an opening 62 extending through its center.

Device 10 includes a second catheter 66 which cooperates with the first catheter, according to an important aspect of the invention, to allow fluid transfer to or from an isolated, selected-length segment of a blood vessel. The second catheter includes a tube 68 having proximal and distal ends, or end regions, 68a, 68b, respectively. As seen in FIG. 3, the cross-sectional area of the tube is substantially less than that of channel 18, and typically about 30-60% less. Tube diameters of between about 20-50 mils are suitable, where the first-catheter tube has the channel dimensions mentioned above.

Figure 5:
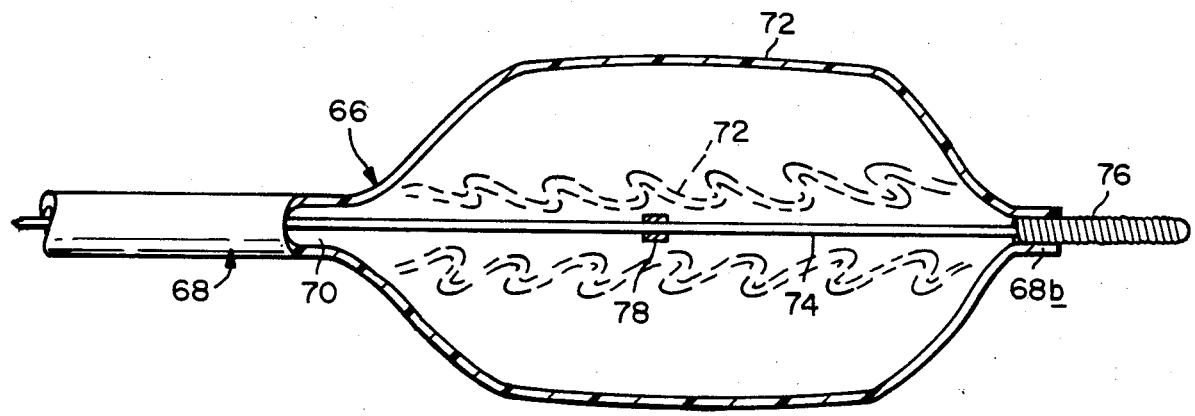
FIG. 5 is an enlarged sectional view taken along line 5—5 in FIG. 1.

Extending through tube is a central bore 70 (FIG. 3) which communicates at its distal end with the interior of an inflatable balloon 72. With reference to FIG. 5, the balloon is formed integrally with the walls of the tube, as an annular, membrane-like segment thereof. The dashed lines in the figure illustrate the pleated configuration which the balloon assumes in its deflated condition. As seen, the deflated balloon has about the same diameter or side profile as the adjacent regions of the tube. The tube, including the integrally formed balloon segment, can be formed by extruding a suitable polymer, such as polyethylene, according to known methods.

A guide wire 74 extending through the bore in tube 68 is used to guide the tube through the channel in tube 16 and into a blood vessel, as will be described. The wire is attached at its distal end to a flexible spring 76, which in turn is secured in the end of bore 70, as seen in FIG. 5. Thus, the wire is securely anchored to the distal end of the tube 68 but can otherwise twist or rotate with respect to the tube along the tube's length. A radio-opague sleeve 78 carried on the wire allows the balloon region of the tube to be monitored fluoroscopically during placement in a blood vessel.

Referring to FIGS. 1 and 2, catheter 66 also includes a two-arm manifold 80 which is connected at its lower end in FIGS. 1 and 2 to the flanged end of tube 68. The manifold has a side port 82 with a conventional syringe fitting, and a central port 84 through which wire 74 is received. Both ports communicate via the interior of the manifold with the inner bore in tube 68, as indicated in FIG. 2. The guide wire and rotating means are also referred to herein collectively as means for guiding the distal end of the second catheter within the first-catheter channel, and in the region distal thereto. Port 82 is used to supply fluid through bore 70 in the catheter, for inflating balloon 72 when the device is operatively placed in a blood vessel.

The proximal end of wire 74 is attached to a wheel 86 which is rotatably mounted on the upper end of the manifold. The wheel mounting allows about two to five full revolutions. An O-ring seal 88 in port 84 is adjustable, by rotation of a thumbscrew 90, to seal the wire in the port. The wheel, wheel mounting, and seal are also referred to therein as means for rotating the guide wire. The particular rotating means shown and described herein is detailed in U.S. patent application for "Low-Profile Steerable Intraoperative Balloon Dilation Catheter". Ser. No. 615,141, filed May 30, 1984, and assigned to Advanced Cardiovascular Systems, Inc. The particular wheel construction is not part of the present invention.

When the device is operatively assembled, as shown in the figures, the inner surface of channel 18 and the outer surface of tube 68 define an interlumen space which forms a passageway 92 (FIG. 3) extending along tube 16 and terminating distally at opening 22 (FIG. 4). The proximal end of the passageway includes the manifold connections between port 54 in manifold 50 and the end of channel 18 in manifold 34, as can be appreciated from FIGS. 1 and 2.

The passageway just described is used in transferring fluid between port 54 and a segment of blood vessel isolated between the two balloons in the device, with such placed operatively in a blood vessel. This is illustrated in the lower portion of FIG. 1, which shows a segment 94 of vessel 12, between balloons 30, 72. The fluid material is transferred into or out of the segment through opening 22 in the device. In this embodiment, where the passageway for transfer of material is formed in catheter 14, the catheter is also referred to as an infusion catheter, and catheter 66, which acts to occlude the distal end of the vessel segment, is also referred to as an occlusion catheter. Alternatively, the passageway for transferring material through the device could be formed in tube 68 in catheter 66, and/or the catheter device could include both such passageways, with suitable modification of the manifolds in the device.

Figure 6:
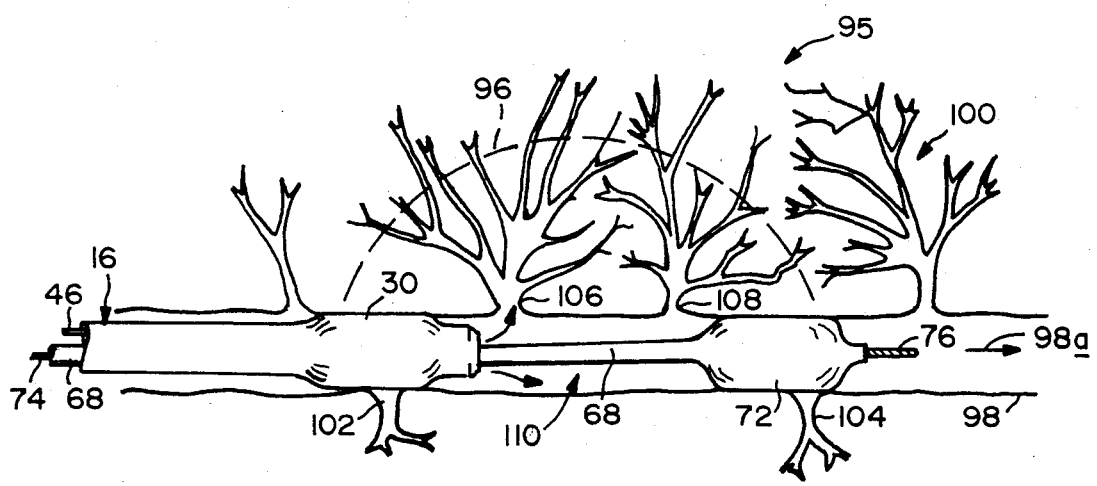
FIG. 6 is a simplified sectional view of tissue, showing the vascular network that supplies the tissue, and the placement of the catheter device for use in transferring a fluid material to or from a selected tissue region, according to the method of the invention.

The operation of device 10 will be described with reference to FIG. 6, which shows anatomical features of a tumor-containing tissue region 95. The upper portion of the tumor is defined by a dashed line 96, and the lower portion, by a supply artery 98 which supplies the tumor with blood. Blood flow through the artery is in the direction of arrow 98a. Normal tissue surrounding the tumor is indicated generally at 100. The tumor and surrounding tissue are supplied blood from a number of smaller arteries or arterial branches, including branches 102, 104 supplying normal tissue on upstream and downstream sides of the tumor, respectively, and branches 106, 108, which feed the tumor. These branches are generally too narrow and too numerous to access directly with a catheter.

According to an important feature of the invention, device 10 is designed to be positioned within the vessel, with balloon 72 located immediately distal to the most distal vascular branch—in this case, branch 108—supplying the target region, and with balloon 30, located immediately proximal to the most proximal vascular branch—here branch 106—supplying the tumor region.

Initially, the individual catheters are individually prepared, by repeatedly infusing and aspirating a balloon-inflation fluid material, such as a contrast agent, until the air in the catheter-tube conduits has been replaced by the fluid material. The first (infusion) catheter is then inserted into a selected percutaneous site, by known catheter methods. To direct the catheter to the selected vessel, such as supply artery 98, a suitable guide wire (not shown), is inserted through the opening in screw 60, and advanced in the catheter until it protrudes from the catheter's distal tip. The wire is then advanced, using fluoroscopy if necessary, until the distal wire end is threaded into the artery of interest, to a point at or near the most proximal target branch artery.

With reference to FIG. 1, the catheter is advanced along the inserted guide wire (not shown) until balloon 30 is positioned just upstream of arterial branch 106. As the catheter is advanced along the wire, its position can be checked, and/or the target branches can be identified or confirmed by periodic injection of contrast material from the catheter, through channel 18. After placing the infusion catheter at the desired location, the guide wire is removed, and hemostasis is provided at screw 60.

To complete placement of device 10 within the selected vessel, the tip of the second (occlusion) catheter is inserted into the opening of screw 60, and the screw is tightened sufficiently to prevent back leakage without appreciably compressing tube 68, i.e., without appreciably restricting relative axial movement of the two catheter tubes. Tube 68 is now guided through tube 16, rotating wheel 86 when necessary to steer the catheter through the tube. (The construction of the device permits twisting of tube 68 with respect to tube 16.) The tube is advanced until balloon 72 is positioned just downstream of the most distal target branch, in the present case, branch 108. It can be appreciated from the figure that the two balloons have been positioned in the vessel with a selected axial spacing which is determined by the distance between selected vascular branches in the tissue of interest. The two balloons in the device are now inflated, typically by injecting contrast material first into balloon 72, then balloon 30, each to a pressure of less than about 40 psi. Complete hemostatic sealing of the isolated arterial segment, indicated at 110 in FIG. 6, can be verified by injecting a bolus of contrast material into the sealed region under fluoroscopy.

The following are some therapeutic and diagnostic methods which are made possible by the device of the invention.

1. Arterial Vaso-Occlusion

The basic operation of the device, in producing occlusion of a selected-length blood vessel segment, has been described above. For use in tumor treatment, the ability to occlude a selected arterial segment, such as segment 110 in FIG. 6, is advantageous as an adjunct to hyperthermic treatment of the tumor. The rationale of this approach is that selectively reduced blood flow through the tumor during hyperthermic treatment can enchance heat-produced damage to the tumor. Heretofore, vessel occlusion at a single site upstream of the tumor tissue has been proposed for tumor treatment by hyperthermia. The present invention allows the tumor to be more effectively isolated from circulating blood.

2. Small-Artery Vaso-Occlusion

Another application of the device is for infusing a vaso-occlusive material into a selected tissue region, to produce occlusion of the small (10–1000 micron) arteries in the tissue. This method, as applied to enhancing the destructive effects of hyperthermia on tumor tissue, is described in U.S. patent application for Hyperthermic Treatment of Tumors, Ser. No. 751,605, filed July 2, 1985, by one of the inventors.

The collagen vaso-occlusive material reported in the above application is prepared by cross-linking a suspension of collagen fibrils with a suitable cross-linking agent, such as glutaraldehyde. Studies reported in the application show that the vaso-occlusion method leads to (a) more rapid heating in occluded tumor tissue, (b) greater heat differential between occluded and non-occluded tissue regions, and (c) slower heat drop after heating, when compared with non-occluded tumor tissue. The present invention contributes to the selectivity of these effects by allowing the vaso-occluded material to be infused into the target tissue in a highly localized manner.

The collagen material is introduced into the isolated segment using conventional fluid injection means, such as a fluid-filled "Angioject" (Advanced Cardiovascular Systems, Inc., Mountain View, Calif.) connected to port 54. The infusion of material into small arteries may be monitored fluoroscopically, by including a suitable contrast dye in the collagen material. Following infusion of the vaso-occlusion material, the isolated arterial region may be drained, by withdrawing material from the segment, to remove occlusion material which might otherwise lead to embolisms. The site of injection can be more thoroughly flushed by alternately draining the segment, and deflating downstream balloon 30 briefly to allow fresh blood to flow into the segment.

The vaso-occlusion procedure just described is suitable for treating a variety of other conditions where localized vaso-occlusion is indicated. Examples include treatment to prevent chronic blood loss resulting from trauma or ulcers, and treatment of vascular problems such as arterial/venous malformation, varices, and hemangiomas.

3. Infusion of Chemotherapeutic Agents

The general approach described above for infusing a solid tumor region with a vaso-occlusive material is applicable to injecting an anti-cancer drug in a tumor. As in the case of vaso-occlusion, the device of the invention allows the drug to be delivered directly to selected arterial branches within a tissue, with drug infusion into adjacent normal tissue. The drug can therefore be administered at higher concentrations, with fewer side effects, than if delivered by a general systemic route.

Another advantage of the drug delivery procedure is the ability to achieve a controlled rate of drug flow into the isolated arterial segment, made possible because the arterial region which receives the drug has a substantially constant, isolated blood volume. The slower flow rate of infused material, by increasing the residence time of the drug, results in an increased drug uptake as the drug passes through the arterial network of the tissue. Flow rates of between about 10% and 90% of normal blood flow rates are readily achievable, using available catheter injection means connected to port 54 of the device. The site can be drained or flushed, as above, following drug administration.

4. Venous-Side Blood Sampling

The catheter device may be positioned similarly in a vein, with the two balloons positioned on either side of the venous branch(es) which drain a localized tissue region of interest. After inflating the balloons, a blood sample from the isolated venous segment is withdrawn through passageway 92, as above. As an example, the method is useful in obtaining adrenal drainage samples for assaying hormone levels.

To remove the device from the vessel site following use, balloon 70 is deflated and the occlusion catheter is pulled back (proximally) until the two balloons are immediately adjacent. After deflating balloon 30, the device is withdrawn as a unit, achieving hemostasis by manual compression.

5. Dissolving Duct Deposits

A catheter procedure for dissolving mineral deposits, such as gall stones, in the gall bladder or bile duct has recently been developed. The procedure involves placing a catheter "behind" the stone and injecting a solvent, such as t-butyl ether, into the duct. One risk in this procedure is that the injected solvent will be carried down the bile duct and drain into the duodenum.

Using the catheter device of the present invention would allow the downstream end of the bile duct to be closed off with balloon 70, whiel balloon 30 would be positioned to block the duct on the other side of the stone(s) to be dissolved. The catheter used would preferably include fluid passageways in both catheters, as described above, to allow solvent lavage, or wash through, in the duct.

From the foregoing, it can be appreciated how various objects and features of the invention are met. The catheter device is readily constructed in part, from known catheter components, and many of the steps involved in the operation of the device utilize available catheter-related appliances, such as those used for in situ placement of the initial catheter, balloon inflation, and injection of fluid material. At the same time, the device allows a number of unique therapeutic and diagnostic applications, related to the ability to localize and isolate, in both upstream and downstream directions, a selected-length vessel segment. These applications and advantages over known catheter methods are discussed above.

While the device has been described with respect to a preferred embodiment, it will be understood that a variety of changes and modifications may be made without departing from the invention.

It is claimed:

1. A catheter device for transferring fluid material to or from a selected-length segment of a vessel, comprising, in operative condition:
   a first catheter having a tube with distal and proximal ends, an inflatable balloon carried adjacent the distal end of the tube, a channel extending through the tube, and a fluid conduit for supplying fluid to the balloon from the tube's proximal end;
   a second catheter having a tube with distal and proximal ends, an inflatable balloon carried adjacent the distal end of the tube, and a fluid conduit for supplying fluid to the balloon from the tube's proximal end, said second-catheter tube and balloon being insertable into and through the first-catheter channel, with such balloon in a deflated condition,;

a fluid passageway formed by an interlumen space between the channel wall in the first catheter and the confronting wall of the tube in the second catheter, and communicating a proximal end region of the first catheter tube with a region between the two balloons, with such placed operatively in the vessel; and means associated with the second catheter for guiding the distal end of the second catheter within said first catheter channel, with the second catheter balloon in a deflated condition, and in the vessel region distal to the first catheter balloon.

2. The device of claim 1, which further includes an annular seal between the two tubes, adjacent their proximal ends, producing a sealing compression which permits relative axial sliding movement of the two tubes.

3. The device of claim 2, wherein the seal includes an O-ring whose sealing compression is selectively adjustable by a thumbscrew.

4. The device of claim 1, wherein the first-catheter tube has an outer diameter of between about 50 and 150 mils, and the second-catheter tube, a diameter of less than about half that of the first-catheter tube.

5. The device of claim 1, wherein the second-catheter tube is an extruded polyethylene tube, and the associated balloon is formed integrally with the tube, as an annular membrane-like segment thereof.

6. The device of claim 5, wherein the second-catheter tube has an outer diameter of between about 20 and 50 mils, and the balloon segment has substantially the same outer diameter as adjacent portions of the tube, with the balloon in a deflated condition.

7. A catheter device for transferring material to or from one or more selected vascular branches of a segment of blood vessel comprising, in operative condition:

a first catheter having a tube with distal and proximal ends, an inflatable balloon carried adjacent the distal end of the tube, a channel extending through the tube, and a fluid conduit for supplying fluid to the balloon from the tube's proximal end;

a second catheter having a tube with distal and proximal ends, an inflatable balloon carried adjacent the distal end of the tube, said tube having a central bore forming a fluid conduit for supplying fluid to the balloon from the tube's proximal end, a central region of the tube between the two tube ends being slidably carried within the channel of the first-catheter tube, to allow placement of the two balloons a selected axial distance from one another on upstream and downstream sides of such selected vascular branches;

the channel wall in the catheter and the confronting wall of the tube in the second catheter, defining an interlumen space which forms a fluid passageway extending through the first-catheter tube, with the device placed operatively in such vessel;

an annular seal for sealing the two tubes adjacent their proximal ends, at a sealing compression which permits relative axial sliding movement of the two tubes;

a guide wire extending through the bore in the second-catheter tube, and secured to the distal end of that tube; and means carried adjacent the proximal end of the second-catheter tube, for rotating the guide wire with respect to the first-catheter tube.

8. A method of transferring a fluid material to or from a selected-length vessel segment defined by proximal and distal ends, said method comprising:

providing a catheter device having (a) a first catheter having a tube with distal and proximal ends, an inflatable balloon carried adjacent the distal end of the tube, a channel extending through the tube, and a fluid conduit for supplying fluid to the balloon from the tube's proximal end, (b) a second catheter having a tube with distal and proximal ends, an inflatable balloon carried adjacent the distal end of the tube, and a fluid conduit for supplying fluid to the balloon from the tube's proximal end, said second-catheter tube and balloon being insertable into and through the first-catheter channel, with such balloon in a deflated condition, (c) a fluid passageway formed by an interlumen space between the channel wall in the first catheter and the confronting wall of the tube in the second catheter, and communicating a proximal end region of the first catheter tube with a region between the two balloons, with such placed operatively in the vessel, and (d) means associated with the second catheter for guiding the distal end of the second catheter within said first catheter channel and in the region distal thereto, inserting the first catheter device into such vessel to position the first catheter balloon at the proximal end of such segment, guiding said second catheter through the channel in the first catheter and into the region distal thereto, to position the second balloon at the distal end of such segment, inflating the balloons, to seal the segment, and transferring fluid material to or from such sealed vessel segment through such fluid passageway.

9. The method of claim 8, for use in treatment of a tumor supplied by arterial branches which are fed by a segment of a supply-artery vessel, wherein said transferring includes introducing a chemotherapeutic agent into the sealed segment between the two balloons.

10. The method of claim 9, wherein said introducing includes injecting such material into the sealed vessel segment at a flow rate which is less than that of the normal blood flow rate through the vessel.

11. The method of claim 8, for use in treatment of a tumor supplied by branch arteries fed by a supply artery, wherein said introducing includes injecting into the sealed segment between the two balloons a collagen vaso-occlusive material adapted to occlude arterial vessels having diameter sizes between about 10 and 500 microns.

12. The method of claim 8, for use in flushing blood and transferred fluid material from such sealed vessel segment, which further includes the steps of withdrawing fluid from the segment, briefly deflating the balloon at the distal end of the vessel, and repeating the withdrawing step.

13. The method of claim 8, for use in dissolving a mineral deposit in a bile duct, wherein the first balloon is positioned in the duct between the deposit and the duodenum, and the second balloon is positioned on the other side of the deposit in the duct.

14. The method of claim 5, wherein inserting the first catheter includes the steps of guiding a wire to the proximal end of the vesesl segment, and advancing the first catheter over the wire until the catheter's distal end is positioned at such proximal proximal-segment end.

15. A catheter device for transferring fluid material to or from a selected-length segment of a vessel, comprising, in operative condition:
- a first catheter having a tube with distal and proximal ends, an inflatable balloon carried adjacent the distal end of the tube, a channel extending through the tube, and a fluid conduit for supplying fluid to the balloon from the tube's proximal end;
- a second catheter having a tube with distal and proximal ends, an inflatable balloon carried adjacent the distal end of the tube, and a fluid conduit for supplying fluid to the balloon from the tube's proximal end, a central region of the tube between the tube ends being slidably carried within the channel of the first-catheter tube, to allow placement of the two balloons a selected axial distance from one another within the vessel; and
- a fluid passageway in one of the two tubes communicating a proximal end region of that tube with a region between the two balloons, with such placed operatively in the vessel.
- wherein the second-catheter tube has a central bore forming the associated fluid conduit in the catheter, and the device further includes a guide wire extending through this bore and secured to the distal end of the tube, and means carried adjacent the proximal end of the second-catheter tube, for rotating the guide wire with respect to the first-catheter tube.

* * * * *